United States Patent [19]

Czeisler et al.

[11] Patent Number: 5,545,192

[45] Date of Patent: *Aug. 13, 1996

[54] INTERMITTENT USE OF BRIGHT LIGHT TO MODIFY THE CIRCADIAN PHASE

[75] Inventors: Charles A. Czeisler; Richard E. Kronauer, both of Cambridge, Mass.

[73] Assignee: Brigham and Women's Hospital, Boston, Mass.

[ * ] Notice: The term of this patent shall not extend beyond the expiration date of Pat. No.5, 304,212. 5,

[21] Appl. No.: 348,257

[22] Filed: Nov. 28, 1994

Related U.S. Application Data

[63] Continuation-in-part of Ser. No. 218,886, Mar. 28, 1994, abandoned, which is a continuation of Ser. No. 97,618, Jul. 27, 1993, abandoned, which is a continuation of Ser. No. 882,172, May 8, 1992, abandoned, which is a continuation-in-part of Ser. No. 819,403, Jan. 10, 1992, Pat. No. 5,304, 212, which is a continuation of Ser. No. 521,041, May 9, 1990, Pat. No. 5,167,228, and a continuation of Ser. No. 365,949, Jun. 15, 1989, Pat. No. 5,176,133, which is a continuation-in-part of Ser. No. 66,677, Jun. 26, 1987, Pat. No. 5,163,426, said Ser. No. 521,041, May 9, 1990, Pat. No. 5,167,228, is a continuation-in-part of Ser. No. 365,949, Jun. 15, 1989, Pat. No. 5,176,133, which is a continuation-in-part of Ser. No. 66,677, Jun. 26, 1987, Pat. No. 5,163,426.

[51] Int. Cl.$^6$ ...................................................... A61N 5/06
[52] U.S. Cl. ................................................................ 607/88
[58] Field of Search ................................................. 607/88

[56] References Cited

U.S. PATENT DOCUMENTS 628,351  7/1899  O'Neill .
720,357  2/1903  Joachimson .

(List continued on next page.)

FOREIGN PATENT DOCUMENTS 2035088  6/1980  United Kingdom .

OTHER PUBLICATIONS

Bio-Brite, Inc. Light Visor™ Product Brochure.
Bio-Brite, Inc. Light Visor™ Instruction Manual, 1992.
"Healthy Food, Exercise Can Help Beat Jet Lag," USA Today Jan. 26, 1993.
Light Glasses™ Brochure by Moodlighters, Inc.
Casano, P., *Light Glasses User's Guide Plus Using Bright Light to Treat Jet Lag*, First Edition (1992).
Circadian Technologies, Inc., 1991 Products and Services Catalog.
Reinberg et al., "Circadian Rhythm Amplitude and Individual Ability to Adjust to Adjust to Shift-Work," *Ergonomics*, vol. 21, No. 10 (1978) pp. 763–766.
Czeisler et al., "Rotating Shift Work Schedules That Disrupt Sleep Are Improved by Applying Circadian Principals," *Science*, vol. 217, No. 4558 (1982) pp. 460–463.
Czeisler et al., "Chronotherapy: Resetting the Circadian Clocks of Patients With Delayed Sleep Phase Insomnia," *Sleep*, vol. 4, No. 1 (1981) pp. 1–21.
Goodwin and Lewy, "The Use of Bright Light in the Treatment of Chronobiologic Sleep and Mood Disorders: The Phase–Response Curve," *Psychopharmacology Bulletin*, vol. 19, No. 3 (1983) pp. 523–525.
Strogartz, *The Mathematical Structure of the Human–Wake Cycle*, Lecture Notes in Biomathematics, No. 69, Springer–Verlag (1986) 239.

(List continued on next page.)

*Primary Examiner*—Ruth S. Smith
*Attorney, Agent, or Firm*—Sterne, Kessler, Goldstein & Fox P.L.L.C.

[57] ABSTRACT

The present invention is a method for modifying the circadian cycle of a human subject to a desired state including the steps of determining the characteristics of the desired circadian cycle, selecting an appropriate time during which to apply a light stimulus to effect a desired modification of the present circadian cycle, and applying the stimulus at the selected time to achieve the desired circadian cycle for the subject. The light stimulus of the present invention includes an episode of intermittent light consisting of at least two pulses of enhanced light separated by at least one pulse of reduced light.

13 Claims, 1 Drawing Sheet

U.S. PATENT DOCUMENTS

| | | |
|---|---|---|
| 730,750 | 6/1903 | Dowsing . |
| 791,232 | 5/1905 | Wolpers et al. . |
| 828,733 | 8/1906 | Fuller . |
| 853,033 | 5/1907 | Roberts . |
| 1,162,424 | 11/1915 | Wiener . |
| 1,222,945 | 4/1917 | Hammerstein . |
| 1,280,857 | 10/1918 | Ruiter . |
| 1,290,036 | 1/1919 | Anderson . |
| 1,337,798 | 4/1920 | Ruiter . |
| 1,563,736 | 12/1925 | Fink . |
| 1,564,552 | 12/1925 | Gerdes . |
| 1,578,654 | 3/1926 | Gerdes . |
| 1,583,420 | 5/1926 | Picard . |
| 1,718,770 | 6/1929 | Zublin . |
| 1,755,418 | 4/1930 | Anderson . |
| 1,842,100 | 1/1932 | Johnson . |
| 1,859,601 | 5/1932 | Rice . |
| 1,951,569 | 3/1934 | Vestvold . |
| 2,008,653 | 7/1935 | Braselton . |
| 2,054,332 | 9/1936 | Lower et al. . |
| 2,114,173 | 4/1938 | Boerstler . |
| 2,184,644 | 12/1939 | Homberger . |
| 2,444,379 | 6/1948 | Sexton . |
| 2,631,588 | 3/1953 | Paschell . |
| 3,042,046 | 7/1962 | Willems . |
| 3,648,706 | 3/1972 | Holzer . |
| 3,773,049 | 11/1973 | Rabichev et al. . |
| 4,100,415 | 7/1978 | Blaisdell et al. . |
| 4,335,724 | 6/1982 | Frei et al. . |
| 4,424,598 | 1/1984 | Cima . |
| 4,444,189 | 4/1984 | Seiverd . |
| 4,469,102 | 9/1984 | Fish . |
| 4,469,951 | 9/1984 | Coco et al. . |
| 4,543,957 | 10/1985 | Freidman et al. . |
| 4,600,723 | 7/1986 | Short et al. . |
| 4,665,086 | 5/1987 | Short et al. . |
| 4,858,609 | 8/1989 | Cole . |
| 4,911,166 | 3/1990 | Leightor et al. . |
| 4,922,930 | 5/1990 | Adkins et al. . |
| 5,006,985 | 4/1991 | Ehret et al. . |
| 5,079,682 | 1/1992 | Roberts . |
| 5,304,212 | 4/1994 | Czeisler et al. ........................... 607/88 |
| 5,327,331 | 7/1994 | Roberts . |
| 5,329,431 | 7/1994 | Taylor et al. . |

OTHER PUBLICATIONS

Lewy et al., "Immediate and Delayed Effects of Bright Light on Human Melatonin Production: Shifting Dawn and Dusk Shifts Dim Light Melatonin Onset," *Annuals*, New York Academy of Sciences (1985) pp. 253–259.

Lewy et al., "Antidepressant and Circadian Phase–Shifting Effects of Light," *Science*, vol. 235, pp. 352–354.

Honma et al., "Phase–Dependent Responses of Human Circadian Rhythms to a Bright Light Pulse: Experiments in a Temporal Isolation Unit," *J. Physiol. Soc.*, Japan (1986) p. 416.

Czeisler et al., "Sleep Deprivation In Constant Light Phase Advance Shifts and Shortens the Free–Running Period of the Human Circadian Timing System," *Sleep Research*, vol. 14, p. 252.

Brown et al., "A Method for Quantifying Phase Position of the Deep Circadian Oscillator and Determining a Confidence Interval," *Sleep Research*, vol 14 (1985) p. 290.

Czeilsler et al., "Entrainment of Human Circadian Rhythms by Light–Dark Cycles: A Reassessment," *Photochemistry and Photobiology*, vol. 34 (1981) pp. 239–247.

Daan et al., "A Functional Analysis of Circadian Pacemakers in Nocturnal Rodents, II. The Variability of Phase Response Curves," *Journal of Comparative Physiology*, vol. 106 (1976) pp. 253–266.

Winfree, *The Geometry of Biological Time*, Springer–Verlag (1980) pp. 36–38, 53.

Saunders, "Circadian Rhythms: Entrainment by Light and Temperature" (Chapter 3), *An Introduction To Biological Rhythms Blackie* (1977) pp. 40–64.

Hoban et al., "Light Effects on Circadian Timing System of A Diurnal Primate, the Squirrel Monkey," *American Journal of Physiology*, vol. 249 (1985) pp. R274–R280.

Daan et al., "Scheduled Exposure to Daylight: A Potential Strategy To Reduce Jet Lag Following Transmeridian Flight," *Psychopharmacology Bulletin*, vol. 20, No. 3 (1984) pp. 566–568.

Wever, *The Circadian System of Man: Results of Experiments Under Temporal Isolation*, Springer–Verlag (1979) 276.

Czeisler et al., "Circadian Rhythms and Performance Decrements in the Transportation Industry," *Proceedings of a Workshop on the Effects of Automation on Operator Performance*, Coblenz, A. M. ed., Commission Des Communautes Europeenes, Programme De Recherche Medicale et de Sante Publique, Universite Rene Descartes: Paris (1986) pp. 146–171.

Kronauer et al., "Mathematical Model of the Human Circadian System With Two Interacting Oscillators," *American Journal of Physiology*, vol. 242 (1982) pp. R3–R17.

Stevens, "To Honor Fechner and Repeal His Law," *Science*, vol. 133 (1961) pp. 80–86.

Czeisler et al., "A Clinical Method to Assess the Endogenous Circadian Phase (ECP) of the Deep Circadian Oscillator in Man," *Sleep Research, vol. 14 (1985) p. 295.*

Wever et al., "Bright Light Affects Human Circadian Rhythms," *European Journal of Physiology*, Pfluegers Archiv. vol. 396 (1983) pp. 85–87.

Wever, "Use of Light to Treat Jet Lag: Differential Effects of Normal and Bright Artificial Light on Human Circadian Rhythms," *Annals New York Academy of Sciences, Part III, Health Effects of Interior Lighting*, (1985) pp. 282–304.

Lingjaerde et al., "Insomnia During the 'Dark Period' In Norther Norway," *Acta Psychiatr. Scand.*, vol. 71 (1985) pp. 506–12.

Lewy et al., "Treatment of Appropriately Phase Typed Sleep Disorders Using Properly Timed Bright Light," *Sleep Research (1985) p. 304.*

Kronauer et al., "A 2–Oscillator Model Derived from Free–running Circadian Rhythms Accurately Predicts Range of Zietgeber Entrainment," *Sleep Research*, vol. 12 (1983) p. 368.

Czeisler et al., "Entrainment of Human Circadian Rhythms by Light–Dark Cycles: A Reassessment," *American Society for Photobiology*, Printed by University of Vermont (1978) p. 73.

Aschoff et al., "Human Circadian Rhythms: A Multioscillatory System," *Federation Proceedings*, vol. 35 (1976) pp. 2326–2332.

Eastman, "Bright Light Improves the Entrainment of Circadian Rhythm of Body Temperature to a 26–Hour Sleep–Wake Cycle in Humans," *Sleep Research* (1986) p. 271.

Ehret et al., *Overcoming Jet Lag*, Berkley Books (New York) (1983) 160.

Arendt et al., "Phase Response of Human Melatonin Rhythms to Bright Light in Antarctica," *Journal of Physiology*, vol. 377 (1986) p. 68.

Kripke et al., "Bright White Light Alleviates Depression," *Psychiatry Research*, vol. 10 (1983) pp. 105–112.

Czeisler et al., "Bright Light Resets the Human Circadian Pacemaker Independent of the Timing of the Sleep–Wake Cycle," *Science*, vol. 233 (1986) pp. 667–671.

Sinclair, and Response by Czeisler et al., "Moonlight and Circadian Rhythms," *Science*, vol. 235 (1987) p. 145.

PCT International Search Report, International Application No. PCT/US88/02177, Search completed on Nov. 3, 1988.

Czeisler et al., "Human Sleep: Its Duration and Organization Depend on Its Circadian Phase," *Science*, vol. 210 (1980) pp. 1264–1267.

Miller, J., "Bright Lights Can Reset the Human Clock," *New Scientist* (Jul. 15, 1989) p. 35.

Long, M. E., "What is this thing called Sleep?," *National Geographic* (Dec. 1987) pp. 786–832.

Lewy et al., "Light Suppresses Melatonin Secretion in Humans," *Sciences*, vol. 210 (1980) pp. 1267–1269.

"Scientists Find Shift Work May Be Hazardous to Heart," *The Washington Post*, Section A8, (Jan. 5, 1992).

"The Latest From the Jet Lag Front," *Travel & Leisure*, Aug. 1994.

Nelson et al., "Sensitivity and Integration in a Visual Pathway for Circadian Entrainment in the Hamster (*Mesocricetus Auratus*)," *Journal of Physiology* 439:115–145 (1991).

Kronauer et al., "Commentary: The Human Circadian Response to Light–Strong and Weak Resetting," *Journal of Biological Rhythms* 8 (4) :351–360 (1993).

INTERMITTENT USE OF BRIGHT LIGHT TO MODIFY THE CIRCADIAN PHASE

STATEMENT AS TO RIGHTS TO INVENTIONS MADE UNDER FEDERALLY SPONSORED RESEARCH AND DEVELOPMENT

This invention was made with government support under Grant Nos. 1RO1AG04912-03 and 1RO1HD20174-01 awarded by the National Institute of Health. The government has certain rights in the invention.

RELATED U.S. APPLICATIONS

This application is a continuation-in-part of Ser. No. 218,886, filed Mar. 28, 1994 now abandoned, which is a continuation of Ser. No. 97,618, filed Jul. 27, 1993 now abandoned, which is a continuation of Ser. No. 882,172, filed May 8, 1992 now abandoned, which is a continuation-in-part of Ser. No. 819,403, filed Jan. 10, 1992, now U.S. Pat. No. 5,304,212, which is a continuation of Ser. No. 521,041, filed May 9, 1990, now U.S. Pat. No. 5,167,228 and Ser. No. 365,949, filed Jun. 15, 1989, now U.S. Pat. No. 5,176,133, both continuations-in-part of Ser. No. 66,677, filed Jun. 26, 1987, now U.S. Pat. No. 5,163,426.

FIELD OF THE INVENTION

The present invention relates to a new and improved method for modifying the circadian cycle of a human subject. More specifically, the present invention relates to a method for modifying the circadian cycle by application of intermittent pulses of bright light.

BACKGROUND OF THE INVENTION

It is known that humans exhibit circadian cycles in a variety of physiologic, cognitive, and behavioral functions. The cycles are driven by an internal biological clock or circadian pacemaker which is located in the brain. It is also known that humans exhibit different degrees of alertness or productivity during different phases of their circadian cycle.

Often, the activities in which humans wish to engage do not coincide with the most appropriate point in their circadian cycle. For instance, transmeridian travelers experience what is commonly referred to as "jet lag", due to the fact that their circadian cycle is not "in tune" with the geophysical time of their destination. In essence, the traveler's physiological cycle either lags or leads their desired activity-rest schedule.

In a similar fashion, people who work in professions requiring them to work at night, such as factory workers, medical personnel, and police experience a desynchrony between the activities in which they desire to engage and their physiological ability to engage in such activities. Commonly known as "shift workers" these individuals often experience an inability to sleep soundly during their non-working hours.

Other sleep-related disorders thought to be related to the misalignment of the circadian cycle with the desired activity-rest schedule include delayed-sleep-phase insomnia, advanced-sleep-phased insomnia and Seasonal Affective Disorder (SAD).

It has been known for quite some time that the circadian cycle of all animals (including humans) is sensitive to exposure to bright light. Thus, it is recognized that the circadian cycle of an animal may be adjusted or modified by exposing the subject to scheduled "pulses" of bright light.

Although all animals are responsive to applications of bright light, the responsiveness of the circadian pacemaker of all animals is not the same. For example, the responsiveness of the circadian pacemaker of a rodent is quite different than the responsiveness of the circadian pacemaker of a human. Indeed, for over twenty years it has been recognized that the response of the circadian pacemaker to light in nocturnal rodents is principally developed during the early time of light exposure (e.g., within the first 15 minutes from the dark-adapted state) while subsequent protracted exposure (e.g., 1–2 hours) generates relatively little additional phase shift. Recently, these findings were considerably sharpened for the case of the golden hamster. See Nelson, D. E. et al., "Sensitivity and Integration in a Visual Pathway for Circadian Entrainment in the Hamster (*Mesocricetus Auratus*),"*Journal of Physiology*, No. 439 (1991), pp. 115–145. A tradeoff between light intensity and stimulus duration was demonstrated (i.e., brighter light requires less duration), and at a modest level of light (e.g., 20 lux) pseudo-saturation of the phase shift response was achieved in about five minutes.

Superficially, the responsiveness of the human circadian pacemaker to light is very different. Unquestionably, humans are less sensitive, requiring several thousand lux of light and stimulus durations of several hours to match rodent phase shifts achieved at 20 lux of light in 5 minutes. This is consistent, however, with the high sensitivity of nocturnal rodents for all visual tasks. It was recently discovered that a significant functional distinction between rodents and humans is the fact that humans appear to sum circadian photic responses progressively. For example, three hours of exposure to bright light produces about ⅗ the phase shift of five hours of exposure to light centered at the same point of the circadian phase.

The apparently disparate functional characteristics of human and rodent responses can actually be described as a manifestation of a single model structure which is the subject of the present invention.

SUMMARY OF THE INVENTION

In accordance with the objectives described above, the present invention is a method of modifying the endogenous circadian cycle of a human subject to a desired state comprising the steps of determining the characteristics of a desired endogenous circadian cycle, selecting an appropriate time with respect to the presumed phase of physiological markers of the subject's present endogenens circadian cycle during which to apply a stimulus to effect a desired modification of the present endogenous circadian cycle, and applying the stimulus at the selected appropriate time to achieve the desired endogenous circadian cycle for the subject. The stimulus comprises an episode of intermittent light consisting of at least two pulses of light of enhanced intensity separated by at least one pulse of reduced intensity.

At least one of the pulses of light of enhanced intensity may be greater than approximately 4,000 lux. At least one of the pulses of light of enhanced intensity may be between 500–1,000 lux. At least one of the pulses of light of enhanced intensity may be between 1,000–2,000 lux. At least one of the pulses of light of enhanced intensity may be between 2,000–4,000 lux. At least one of the pulses of light of enhanced intensity may be between 4,000–100,000 lux.

At least one of the pulses of light of reduced intensity may be between 0–200 lux. At least one of the pulses of light of reduced intensity may be between 0–10 lux. At least one of the pulses of light of reduced intensity may be between 10–50 lux. At least one of the pulses of light of reduced intensity may be between 50–200 lux.

The episode of intermittent light may comprise a 5-hour episode of approximately 25-minute cycles, each 25-minute cycle including a 1-minute transition up to light of enhanced intensity, four minutes of enhanced light, a 1-minute transition down to light of reduced intensity and 19-minutes of light of reduced intensity. Approximately 20% of the duration of the episode of intermittent light may be light of enhanced intensity.

In another aspect, the present invention is an apparatus for applying a light stimulus to a human subject to achieve a desired endogenous circadian cycle comprising an enhancing means for exposing the subject to light of enhanced intensity, a reducing means for exposing said subject to light of reduced intensity and a controlling means for controlling exposure of the subject to light of enhanced intensity and light of reduced intensity. The apparatus may also include a photosensor. The apparatus may be incorporated into a pair of eyeglasses or a visor.

BRIEF DESCRIPTION OF THE DRAWINGS

The method of the present invention is best understood and appreciated by referring to the accompanying drawings in which.

DETAILED DESCRIPTION OF THE INVENTION

Several methods for assessing and modifying the circadian cycle of a human subject are disclosed and claimed in the patents and applications listed in the RELATED U.S. APPLICATIONS section of this document. The disclosures of the listed patents are incorporated, in their entirety, into the present application by reference. While the circadian cycle of a human subject may be successfully assessed and modified by the methods disclosed in each of these patents, subsequent research has shown that the circadian cycle may be modified more efficiently by a model based on a photic transducer which reflects the recent finding that humans appear to sum circadian photic responses progressively.

Although not fully addressed in the present disclosure, it must be remembered that prior to modifying the circadian phase of a human subject to a desired state, the present circadian cycle of the subject must first be assessed. The subject's present circadian cycle may be successfully assessed using any of the techniques disclosed in the patents previously listed in this document and such assessing techniques are specifically incorporated into the present disclosure by reference.

Figure 1:
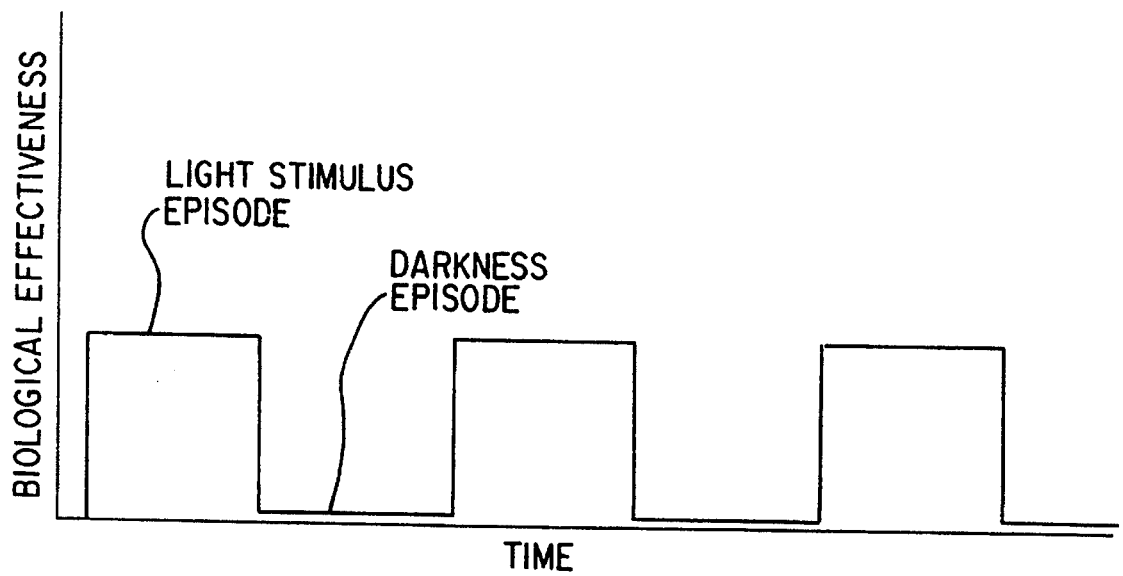
FIG. 1 is a graphic representation of what was thought to be the response of the circadian pacemaker to pulses of enhanced and diminished light.

Prior to discussing the improved model of the present invention, it may be helpful to briefly discuss the development of circadian models over the past several years. It was originally thought that in order to rapidly shift the circadian phase the subject must be exposed to a bright light stimulus of high intensity (e.g., 10,000 lux) for a long period of time (e.g., 5 hours). As shown in FIG. 1, it was believed that the circadian pacemaker was immediately responsive to exposure to light and that such a level of responsiveness was maintained until exposure to the light stimulus was interrupted. As the light stimulus was interrupted, it was thought that no further response of the circadian pacemaker could be evoked and that the circadian pacemaker was instantaneous in nature, as its responsiveness to a light stimulus was initiated and terminated precisely with the timing (or onset and offset) of the light stimulus.

Figure 2:
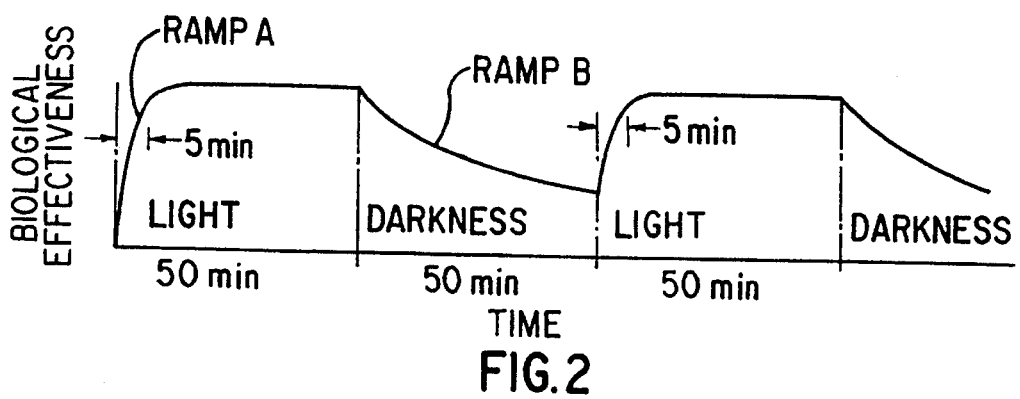
FIG. 2 is a graphic representation of a second theory as to how the circadian pacemaker responded to pulses of enhanced and diminished light.

Subsequent research indicated, however, that the circadian pacemaker did not respond to light stimuli as previously thought. With reference now to FIG. 2, a second theory was developed which was based on the premise that an increase in retinal light exposure requires a measurable duration of time (time ramp A) to initiate the neurophysiologic or neurohumoral chain of events responsible for mediating the circadian response to enhanced light exposure and that these biological effects of enhanced light on the circadian pacemaker will persist on a diminishing trajectory (time ramp B) for some duration of time following a reduction in the level of retinal light exposure. Thus it was thought that the circadian pacemaker continued to respond on a diminishing scale to the previous light stimulus even though the subject was being exposed to an episode of darkness (or an interruption of the light stimulus that need not be total darkness). Based on this perceived response of the circadian pacemaker, it was thought that intermittent exposure to bright light could be nearly as effective as continuous exposure to bright light.

While it is true that intermittent exposure to bright light can be nearly as effective as continuous exposure to bright light, the representation of the responsiveness of the circadian pacemaker as shown in FIG. 2 was not accurate. On the contrary, it has been recently discovered that the circadian pacemaker responds to light stimuli in the manner shown in FIG. 3 and that only intermittent pulses of light are required to effectively shift the circadian phase.

Figure 3:
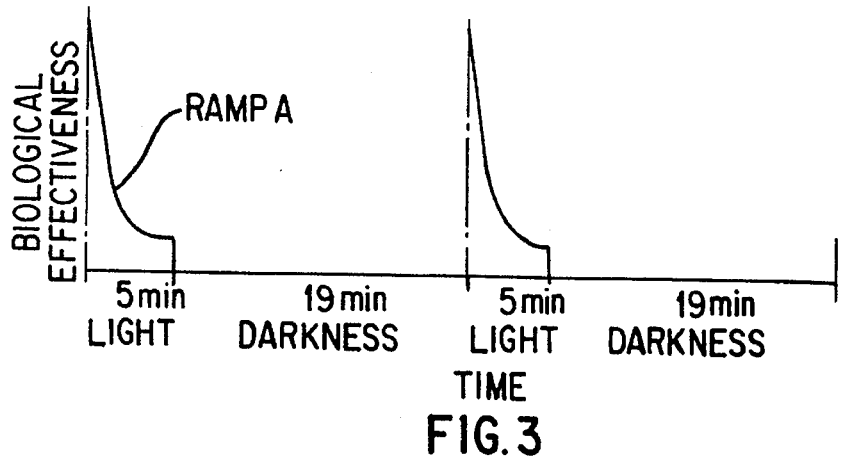
FIG. 3 is a graphic representation of the response of the circadian pacemaker to pulses of enhanced and diminished light based on the photic transducer model of the present invention.

The response curves of FIG. 3 are based on studies performed where the subjects were exposed to 5 hour episodes of an intermittent light stimulus with only 5 minutes of enhanced light per 25 minute cycle. Each 25 minute cycle consisted of 1 minute of transition up to enhanced light, a four minute pulse of enhanced light, 1 minute of transition down to darkness, and a 19 minute pulse of darkness. The phase shifts of those exposed to this intermittent light stimulus were approximately half of those seen when giving subjects 5 hours of continuous lighting, even though the subjects were exposed to light for only 20% of the episode of the light stimulus.

Referring now to FIG. 3, it can be seen that during the first 5 minutes of the stimulus cycle the responsiveness of the circadian pacemaker is initially high, but subsequently declines throughout the duration of the 5 minute stimulus pulse. During the 19 minute pulse of darkness, no response of the circadian pacemaker is evoked. When the 5 minute light stimulus pulse is resumed, the response of the circadian pacemaker is again initially high and subsequently declines throughout the duration of the 5-minute stimulus pulse. With the onset of the second 19 minute darkness episode, the circadian pacemaker again becomes unresponsive.

The responsiveness of the circadian pacemaker to light (as shown in FIG. 3) is based on the phenomenon of a "photic transducer" which is comprised of a population of neuronal elements which are responsive to light for a limited time period to "drive" or shift the circadian pacemaker. These elements are not perpetually responsive to light, as these elements are "burnedup" or "spent" after an exposure period to light. This burning up of neuronal elements is illustrated in FIG. 3 by downward sloping response ramp A which elapses during the first 5 minutes of the stimulus episode. After a certain period of time (which occurs during the darkness episode) these elements are "recycled" at a predetermined rate, so that they are once again responsive to light during the application of the second 5 minute light stimulus pulse. The dynamic photic transducer briefly described above with respect to FIG. 3 is embodied in the improved method of the present invention and will now be described in more detail below.

To accommodate the pseudo-saturation found in rodent responses, the improved model of the present invention postulates a finite population of potentially active neuronal elements that, in the absence of light, I, are inactive, but are ready to be activated. These are said to be in the "ready" state. Exposure to light activates these neuronal elements. Activation of any particular element is a probabilistic process and we let $\alpha(I)$ represent the rate at which activation occurs for the population (i.e., the fraction of the "ready" elements activated per minute). The stronger I is, the larger $\alpha$ is. When activated, each element rapidly initiates a chain of chemoelectric events which delivers a "quantum" of drive to the circadian pacemaker, whereupon the element is used-up and enters a subpopulation called "spent" elements. A recycling process restores the "spent" elements to the "ready" state at a rate $\beta$(the fraction of "spent" elements that are recycled per minute) which is independent of the light intensity I.

This population of elements constitutes a dynamic photic transducer which receives the light intensity pattern I(t) as an input and delivers quantal flux, $\delta(t)$ as drive to the circadian pacemaker. In the present model, the drive to the pacemaker depends on the history of I(t), not simply its current value.

Letting n represent the fraction of all elements which are "spent" at any given time, then (1−n) represents the fraction which are "ready". The described rate processes lead to the differential equation $$\frac{dn}{dt} = (1-n)\alpha - n\beta \quad (1)$$

Any protracted light level, $\bar{I}$, will give a constant value for $\alpha(\bar{I})$ and, in time, n will achieve a steady level, $\bar{n}$:

$$\bar{n} = \frac{\alpha(\bar{I})}{\alpha(\bar{I}) + \beta} \quad (2)$$

In particular, if $\bar{I}=0$ we expect $\alpha(\bar{I})=0$ and $\bar{n}=0$. That is, in the absence of photic stimulation all elements revert to the "ready" state. For a steady $\bar{I}\neq 0$ there will be a steady rate, $\bar{\delta}$, at which quanta are delivered to the pacemaker (the continuing rate at which recycled elements are activated). The drive rate onto the pacemaker may be represented as $$\begin{aligned}\bar{\delta} &= \hat{C}\alpha(\bar{I})(1-\bar{n}) = \hat{C}\frac{\beta\alpha(\bar{I})}{\alpha(\bar{I}) + \beta} \\ &= \hat{C}\beta\bar{n}\end{aligned} \quad (3)$$

where the coefficient $\hat{C}$ is the product of the absolute number of elements and the absolute drive strength of each quantum. The right-hand-side of equation (3) has the standard form of the logistic function (sometimes called the Naka-Rushton function or the Michaelis function). However large the activation rate $\alpha$ may be, $\bar{\delta}$ can never exceed $\hat{C}B$. In physical terms, when $\alpha\gg\beta$ almost all the elements are in the "used"

state (n≅1) and it is the recycle rate that limits the rate at which elements can be continuously reactivated.

A most important feature of the photic transducer is its transient response to the switching-on of light after extended darkness when essentially all of the elements are in the "ready" state. Letting time, t, be zero at the switch-on to light intensity, $\bar{I}$, the transient is given by $$n(t)=\bar{n}(1-e^{-(\alpha(\bar{I})+\beta)t}) \quad (4)$$

$$\delta(t)=\hat{C}(1-n(t))\alpha(\bar{I})=\hat{C}\beta\bar{n}+\hat{C}\alpha\bar{n}^{-(\alpha(\bar{I})+\beta)t} \quad (5)$$

The right-side of equation (5) conveniently separates into two terms. The first term is what would be expected from the steady-state drive rate alone. We will call this the "sustained response" rate, $\delta_{sustained}$. The second term represents the rapid activation of the reservoir of "ready" elements which accumulated during the preceding darkness. We will call this the "acute response" rate (to an acute stimulus), $\delta_{acute}$. If the light remains at $\bar{I}$ for some duration of time so that $(\alpha(\bar{I})+\beta)t\gg 1$, the acute response will die out. The cumulative drive due to the acute response is $$\int_0^\infty \delta_{acute}\, dt = \hat{C}\bar{n}^2 \quad (6)$$

The cumulative acute response "saturates". If the stimulus is applied for a duration, T, the cumulative sustained drive is simply $$\int_0^T \delta_{sustained}\, dt = \hat{C}\beta\bar{n}T \quad (7)$$

The cumulative sustained drive will equal the cumulative acute drive for a time, T, which we denote by $T_{critical}$:

$$T_{critical}=\bar{n}/\beta \quad (8)$$

The significance of this critical time value is that for stimulus duration shorter than $T_{critical}$ the acute component dominates the response while for durations longer than $T_{critical}$ the sustained component dominates. With this model the pseudo-saturation of rodent response corresponds to a dominance of the acute component while the proportionality of response to stimulus duration seen in humans corresponds to a dominance of the sustained component. For strong stimuli, so that $\alpha(I)\gg\beta$, n≅1 and $T_{critical}$ is dictated by $\beta$. We conclude that $\beta$ for humans is considerably larger than for rodents.

It is equally important to understand the prediction of this photic transducer model in the case where a sustained light stimulus is interrupted by an episode of darkness (I=0). Let the darkness begin at t=0 and last for a duration, T. Before and after the darkness the light has intensity $\bar{I}$ for which the corresponding $\bar{n}$ is given by equation (2). Since I=0 implies $\alpha=0$, no further activations from the "ready" state occur once darkness is initiated. Consequently the drive onto the pacemaker, $\delta$, is zero throughout the dark episode $0\leq t\leq T$. However, the "spent" elements continue to be recycled during darkness, so n decreases and the fraction of "ready" elements, 1−n, increases:

$$n(t) = \bar{n}e^{-\beta t} \quad (9)$$

$$1 - n(t) = 1 - \bar{n}e^{-\beta t} \quad 0 \leq t \geq T$$

When the light is once again brought up to $\bar{I}$ at the end of the dark episode there will be an acute drive component in addition to the sustained drive. For t>T we have $$\delta(t) = \hat{C}\beta\bar{n} + \hat{C}\alpha(\bar{I})\bar{n}[1-e^{-\beta T}]e^{-(\alpha(\bar{I})+\beta)(t-T)} \quad (10)$$

for which the cumulative acute drive is $$\int_T^\infty \delta_{acute}\,dt = \hat{C}\bar{n}^2(1-e^{-\beta T}) \quad (11)$$

During the dark episode there is a cumulative loss of sustained drive given by $\hat{C}\beta\bar{n}T$. This loss is partially offset by acute drive which occurs when $\bar{I}$ is brought back.

The net loss is then $$\hat{C}\beta\bar{n}T - \hat{C}\bar{n}^2(1-e^{-\beta T}) \quad (12)$$

$$\hat{C}\bar{n}\beta T\left[1 - \bar{n}\frac{(1-e^{-\beta T})}{\beta T}\right]$$

For $\beta T \ll 1$ and a strong stimulus (so $\bar{n} \cong 1$) the net loss of drive is very small. This explains how there may be very little penalty for turning off the stimulus completely for moderately long episodes provided light is subsequently reinstated and the increased pool of "ready" elements is utilized. Moreover, this model makes a specific prediction of the manner in which the loss of drive depends on the duration of the episode of darkness. The value of the recycle rate, $\beta$, can be estimated from a single experiment as described in detail below. The functional form can be validated by a series of experiments with varying duration of darkness or diminished light.

It should be understood that the intensity of light during a pulse of enhanced light exposure may fall within a variety of ranges. For example, the intensity of a pulse of enhanced light could fall within a variety of ranges, including ranges of approximately 500–1,000 lux; 1,000–2,000 lux; 2,000–4,000 lux; and 4,000–100,000 lux. As stated previously, as the intensity increases the light stimulus pulse would be able to activate more neuronal elements.

The intensity of light during a pulse of reduced or diminished light exposure may also fall within a variety of ranges. For example, the intensity of a diminished light stimulus could fall within the range of approximately 0–200 Lux; 0–10 lux; or 50–200 lux.

Nothing in the foregoing disclosure is intended to limit the intensity range of an enhanced or diminished light stimulus to the intensity ranges enumerated above. The key to determining whether a particular intensity of light should be characterized as "enhanced" or "diminished" with regard to a particular subject is the effect of that light intensity on the circadian rhythm of the particular subject to which it is applied, as well as the length of the pulse.

Experiments to Evaluate Rate Parameters, $\alpha(I)$ and $\beta$

Due to the "noise" in the assay of human circadian phase (random fluctuations of temperature) experiments should be designed to produce anticipated phase shifts of a few hours, at least. Consequently bright light stimuli are commonly extended for 5 hours. Based on the evidence that response is approximately proportional to stimulus duration when 3 hour and 5 hour durations are compared, it is clear that in model terms both 3 hour and 5 hour $\gg T_{critical}$. The magnitude of $T_{critical}$ (and consequently the size of $\beta$) can best be estimated by embedding darkness episodes of duration approximately equal to $T_{critical}$ within the total stimulus window. The loss of cumulative drive (evidenced as reduced phase shift compared to that achieved with no darkness episodes) leads to an estimate of $\beta$ via equation (12).

To enhance the phase shift reduction and thereby improve experimental accuracy, several darkness episodes should be embedded within the stimulus window, provided the duration of brightness between the dark episodes is long enough to return the elements to the steady-state level where the fraction of spent elements is $\bar{n}$, implying that the full cumulative acute drive given by equation (11) is realized. This means that the duration of light between the dark episodes should be long compared to the $(\alpha(I))^{-1}$. Since we expect $\alpha \gg \beta$, this full realization of the acute drive should be achieved if the intervening light episodes are also approximately equal to $T_{critical}$.

Once the estimate of $\beta$ is obtained from experiments in which the stimulus consists of light and darkness episodes of approximately equal duration, the value of $\alpha(I)$ can be assessed by a pattern of interspersed light and dark episodes within the stimulus window in which the duration of light episodes is brief (somewhat less than $(\alpha(I))^{-1}$ so that acute response is not fully realized. The dark episodes should have a duration about half of $T_{critical}$ so that reduction of phase shift, when it occurs, can be ascribed to incomplete acute response.

As postulated, the activation rate, $\alpha$, depends on I and so too does the sustained drive rate $\delta$ with a line (see equation (8)). By comparing phase shifts produced by 5 hour stimuli of different intensity (for which the acute component represents little of the total drive) we are approximately comparing the sustained drive rates at the different intensities. Equation (3) enables us to infer the corresponding $\alpha(\bar{I})$. In a wide variety of studies of phototransduction where data are fit by a logistic function such as equation (3) it has proven useful to let $$\alpha(I) = (I/I_o)^p \quad (13)$$

wherein $I_o$ establishes the reference intensity for which $\alpha=1$ (in whatever units of time have been chosen; minutes here) while the exponent p is typically less than 1 and usually in the range $0.6 \leq p \leq 0.9$. For humans, we estimate $p=0.85$ and $I_o=30,000$ lux. (These parameters are estimated by fitting phase shift data at various light intensities with the logistic equation (2). The value of $\beta$ is found from experiments in which light and dark episodes alternate within the stimulus window.) With I=30,000 lux, the activation rate, $\alpha$, will be $1\,\text{min}^{-1}$. For comparison, the hamster data from Nelson et al. are best fitted by $p=0.6$ and $I_o=10$ lux, the latter corresponding to the enhanced visual sensitivity of rodents vis-a-vis humans.

In neuronal processes, response to a stimulus often is found only after some threshold stimulus is attained. We anticipate that at very low levels of I the transition rate $\alpha(I)$ may be zero, so that only after I is raised to some critical level will any response be observed. Since, in a population of potentially active neuronal elements the individual elements would very likely have different threshold levels, distributed statistically, the transition between $\alpha(I)=(I/I_o)^p$ and $\alpha(I)=0$ will not be abrupt. There is evidence that hamster response has a threshold at about 0.1 lux. Human response shows no threshold behavior for I as low as 150 lux.

We have performed experiments in which a single 5 hour stimulus is subdivided into 4 bright light (10,000 lux) episodes with three interspersed dark (less than 1 lux) episodes all of approximately equal duration ($\cong 42$ minutes). From these we have inferred that the recycle rate, $\beta$, is approximately $0.02\,\text{min}^{-1}$. No other comparable experiments for hamsters are known, but by comparing phase shifts obtained (by various investigators) with sustained light durations of 5, 10, 15, and 60 minutes, we infer that $\beta$ is approximately 0.01 min$^{-1}$ or about 50% of the human recycle rate.

Photic Transducer Model Summary

The essential equation is (1)

$$\frac{dn}{dt} = (1-n)\alpha - n\beta \qquad (1)$$

The activation rate constant $\alpha$ is a function of I for which we have selected the form $$\alpha(I) = (I/I_o)^p \qquad (13)$$

where $I_o$ and p are constants. For any specified temporal pattern of light, I(t), equation (13) gives $\alpha(t)$. Integration of equation (1) gives n(t). The drive onto the pacemaker is then given by $$\delta(t) = \hat{C}(1-n(t))\alpha(t)$$

In general the integration of (1) must be done numerically. Selected analytic integrals for I(t) that change stepwise have been developed above.

The present best estimates for model parameters are
$\beta = 0.02$ min$^{-1}$
$I_o = 30,000$ lux (with $\alpha$ measures in min$^{-1}$)
$p = 0.85$
The coefficient $\hat{C}$ is evaluated by making the steady drive, $\bar{\delta}$, for 10,000 lux match the value $B = CI^{1/3} = 0.018 (10,000)^{1/3} = 0.388$, of the direct-drive model:
$\alpha(10,000) = (\frac{1}{3})^{0.85} = 0.393$ min$^{-1}$
$\bar{n}(10,000) = 0.393/(0.393 + 0.02) = 0.952$
$\hat{C} = 0.388/(1-0.952)(0.393) = 11.0$

Further Signal Processing

The photic transducer model described above very simply encompasses two of the most important nonlinear aspects of the response of the circadian pacemaker to photic stimulation. One is the temporal pseudo-saturation seen in those animals for which the pacemaker drive is dominated by the acute component. The other is the intensity saturation effect found in the sustained component (see equation (2)) and evidenced in human response that is typically dominated by sustained drive effects.

It is useful to examine the consequences of interposing a linear temporal filter between the photic transducer output, $\delta(t)$, and the pacemaker. One of the simplest filters is described by a first-order differential equation, $$T_f \frac{dB}{dt} + B = \delta(t) \qquad (14)$$

where B is the filter output (and hence represents the drive onto the pacemaker). $T_f$ is the filter time constant. This filter has the properties of smoothing the $\delta(t)$ and, in an approximate sense, delaying the smoothed version by $T_f$. The long-time integral of B is equal to that of $\delta$, so the integrated strength of the drive to the pacemaker is unchanged by the filter. In the case of a hamster exposed to a 5 minute pulse of 20 lux of brightness, the acute response of $\delta(t)$ will be essentially complete at the end of the pulse. Moreover, the turning-off of the light at the end of the pulse means that no further drive can be generated. The interposition of a filter of the type described implies that the filter output drive to the pacemaker, B, may be considerably extended, declining exponentially with a time constant $T_f$.

A very interesting situation arises if $T_f$ is matched to the recycle rate constant $\delta$:

$$T_f = \beta^{-1}$$

Equation (1) can be simply rearranged $$\frac{dn}{dt} + \beta n = (1-n)\alpha \qquad (1)$$

so that the right side is exactly $\delta(t)$. The left side can be rewritten $$T_f \frac{d(\beta n)}{dt} + \beta n = \delta_n(t) \qquad (15)$$

comparison of equation (15) with equation (14) shows that in this special case $$B = \beta n \qquad (16)$$

That is, the output of the matched filter is equal to n (the fraction of "spent"e elements) multiplied by the recycle rate constant, $\beta$.

The combination of the photic transducer with following matched filter leads to a second model interpretation. In this interpretation, we suppose that transducer elements, upon activation, enter a state of sustained drive onto the pacemaker (rather than delivering only a quantum of drive). In such a case, the drive to the pacemaker at any time will be proportional to n (the fraction of elements which have been activated). The recycle rate, $\beta$, now represents the rate at which active elements cease being active. In this view, when an episode of light is initiated from a state of protracted darkness, the drive to the pacemaker will progressively increase as elements are activated (moved to the state represented by the fraction n) up to the level $\bar{n}$. When the light is then turned off, drive to the pacemaker will continue while the fraction n declines exponentially with the time constant $\beta^{-1}$. This model may be called an "element recruitment" model wherein the "ready" elements are recruited into extended activation. Equations (15) and (16) show that the "expenditure" model with the matched filter added is the mathematical equivalent of the "recruitment" view.

The question of whether a filter such as (14) exists in the signal pathway is difficult to appraise experimentally and is largely moot. First, the response processes within the pacemaker itself are integrative, and so change very little with input signal smoothing. Secondly, any delay produced by the filter can simply be accommodated as a change in the presumed timing of the phase response curve (PRC) relative to other circadian markers. Only when the physiology of the internal pacemaker mechanism is elucidated can this question be properly addressed It is important to observe that light input mediating other biological effects such as melatonin suppression or alertness enhancement may operate via the same photic transduction mechanism as that which mediates effects on the circadian pacemaker.

Significance of Representation of Photic Transducer Function

Heretofore, the conventional view of the action of light on the circadian pacemaker implied that a brief reduction of stimulus (such as might be produced by directing one's gaze away from a bright light source) would invoke a penalty in the cumulative stimulus effect. Through a series of experiments employing unique temporal patterns of bright and dark episodes contained within the overall stimulus time-window we have demonstrated that even long (e.g., 30 minute) intervals in which light is completely absent can be accommodated with relatively little penalty, provided these are followed by sufficiently long (e.g., 5–10 minute) episodes of bright light. This discovery greatly enhances the applicability of bright light interventions in the workplace, in phototherapy routines and for personal use (for example, in preventing jet lag). For example, in industrial situations where the job may call for some duties in a dark or dimly lit environment, the use of bright light to produce adaptation to shift rotation need not be compromised.

Since the required duration of bright episodes is related to the activation rate, $\alpha$, which is itself strongly dependent on light intensity, I, the prescription for temporal light patterning changes with the brightness of available light. The mathematical representation of the photic transducer permits an optimal accommodation to any imposed limitations of brightness or work schedule.

Based on prior modelling work, it is known that for extended durations of light exposure (e.g., 3 to 5 hours) the penalties to be paid by lowering light intensity from about 10,000 lux to 3,000 lux were modest. The relationship $B=CI^{1/3}$ predicts only a 33% decrease in drive to the pacemaker for this more than threefold reduction of light intensity. Recent data at 1250 lux imply the decrease in pacemaker drive is even smaller than this prediction. Seemingly, there is little profit in pursuing very large I. However, transducer models shows that when intermittent bright light patterning is considered, 10,000 lux actually has a very special advantage over 3,000 lux, by allowing a much lower fraction of rime during which the light need Be applied to provide a desired effect (known as a shorter "duty cycle"). One simple consequence that can be deduced from the model is that if all light and dark episodes are Brief (i.e., less than about 1 minute) the her effect is equivalent to a steady intensity whose $\alpha$value is that of the actual reduced By the fraction of time that the light episodes represent.

For example, if 10,000 lux is viewed for 50% of the rime (and darkness for the other 50%), the equivalent steady intensity is that for which $\alpha\frac{1}{2}$ times $\alpha(10,000)$. Using the exponent p=0.85 gives an equivalent steady intensity of 4,400 lux. Put another way, the availability of 10,000 lux allows a duty cycle of 0.5 (for rapid intermittence) with the equivalent of 4400 lux. With our current estimate of photic transducer parameters, equations (2) and (3) predict that the loss in drive to the pacemaker will Be less than 5%. A similar calculation for a duty cycle of 0.2 (20% of at 10,000 lux and 80% of the time at 0 lux) gives an equivalent steady I of 1,505 lux and a reduction of pacemaker drive of 16%.

Devices Capable of Utilizing the Photic Transducer Model of the Present Invention The use of intermittent light schedules offers a special opportunity for devices by means of which a person can monitor the status of his/her photic transducer. In particular, by monitoring light exposure with a tiny ambulatory lux meter and feeding such data to a special purpose microcomputer that integrates equation (1), the user can obtain on-line an output portraying both the correct level of "ready" and "spent" elements and also the cumulative drive delivered to the circadian pacemaker from any chosen start time. If the user has remained away from suitably bright light for too long a time, a warning reminder can be sounded. In this way, the user can achieve desired objectives for manipulating the circadian pacemaker (both Type 1 and Type 0) resetting) without personal attention to minute-by-minute light exposure. Moreover, it is seldom that intermittent light patterns will be a simple mixture of bright episodes and totally dark episodes. Rather, a continuous pattern of variations from quite bright to quite dim light will be more common, and online computation is almost essential to avoid serious stimulus lapses which could strongly reduce cumulative drive. This is especially important where light in evening hours is called for, since normal environmental light is not strong and serious effort is required to access bright light.

At a higher level, the measured pacemaker drive can be applied to a computer replica of the pacemaker itself and the overall phase and amplitude status of the pacemaker displayed. Those capabilities are especially important if the user is planning to achieve maximum phase shifting effects by type 0 resetting (i.e., suppression of circadian amplitude en route to the final desired state). It should be remembered that efficient resetting of the circadian pacemaker requires avoidance of light drive at certain times as well as strong delivery of light at other times. If a computer replica of the pacemaker is available and the resetting objectives are read in, an output indicating when light is to be avoided can be easily generated. When combined with the aforementioned photosensor, warning signals can be produced. This can be important since the photic transducer model implies that relatively brief (e.g. a few minutes) exposure to unwanted light can produce significant adverse drive to the pacemaker.

The computation that monitors the ready/spent status of the photic transducer operates on a time scale of minutes to a few hours. The computation that estimates the status of the circadian pacemaker itself is necessarily operating on the circadian time scale.

The improved method described herein may be applied to other settings or devices to efficiently effect modification of the circadian phase. For example, a lounge used by shift workers could be equipped with bright lights and a timing device which has been programmed in accordance with the improved model of the present invention.

Another example of an application of an intermittent light stimulus would involve a pair of eyeglasses with means for exposing the wearer to light of selected intensity at selected times. Such eyeglasses could be used, for example, by those travelling across time zones or by shift workers. Because the light source would be close to the eyes of the wearer, and because the light stimulus would be intermittent, very little power would be required for such a device. A similar light emitting device could be similarly incorporated into a visor or hat.

Yet another example of an application of the method of the present invention would be to mount a light source and a control mechanism onto the headboard of a bed, or other lounging location where the user is likely to be when the light stimulus is to be applied. It is envisioned that such a device could be small enough to be carried by a traveler, for example.

The method of the present invention may be further applied to any of the devices disclosed in the parent patents described at the beginning of this application, the disclosures of which being incorporated in their entirety herein by reference.

Theoretical Foundations for Modifying the Circadian Phase and Amplitude

The endogenous (deep) circadian pacemaker, hereafter designated as "the x oscillator," or simply "x," may be modelled mathematically by a second-order differential equation of the van der Pol type, specifically:

$$(12/\pi)^2 \frac{d^2x}{dt^2} + m_x(-1+4x^2)\frac{12}{\pi}\frac{dx}{dt} + (24/\tau_x)^2 x = F_x$$

In the absence of any forcing function, $F_x$, x will have an approximately sinusoidal waveform with an amplitude of 1 (that is, the full excursion of x from a maximum of +1 to a minimum of −1 will be 2).

The forcing function, $F_x$, consists of two effects. The dominant effect is that of the light to which the retina is exposed. The secondary effect is due to endogenous internal influences of the activity-rest pattern.

In the form given above, time t is measured in clock hours. The parameter $m_x$ is the "stiffness" of the x oscillator and for normal humans is expected to be in the range $0.05 \leq m_x \leq 0.15$ with 0.1 as the representative value. The estimate of 0.1 for $m_x$ was originally chosen as a trial value by analogy with the value of $m_y$ (the internal "stiffness" of the y oscillator) of our dual oscillator model of the human circadian timing system which had been validated by earlier experimentation characterizing a phenomenon called phase trapping. Our experimental success in manipulating the amplitude of the oscillatory output implies that $m_x$ is very unlikely to be larger than 0.15, and certainly not larger than 0.2. An oscillator with an internal stiffness coefficient less than 0.03 would be unreasonably susceptible to external influences and therefore physiologically incompatible with the observed robustness of the endogenous circadian ("x") oscillator sensitive in this context. The parameter $\tau_x$ represents the intrinsic period of the x oscillator and for normal humans is expected to be in the range $23.6 < \tau_x \leq 25.6$ with 24.6 as the representative value.

For most people in the age range 5 to 55 years, sleep occurs in a single consolidated episode each 24 hour day. In the laboratory paradigm of "free run" (self-selected sleep and wake) the sleep/wake cycle time for young adults is typically in the 25 to 26 h range. About 30% of free run experiments lead spontaneously to internal desynchrony in which the sleep/wake cycle time exceeds 30 hours (ranging up to 50 hrs) while the core body temperature rhythm proceeds at about 24.5 h. We ascribe these separate rhythms to distinct rhythm generators: y for the labile sleep/wake process and x for the "deep circadian pacemaker". In synchronized free run the interactions between y and x produce mutual entrainment, and since the compromise cycle time, $\tau$, is biased strongly toward $\tau_x$, it follows that the action of y on x is only about 25% of the action of x on y.

Enhanced Model

In its simplest form, the model is $$\dot{X} = \frac{\pi}{12}\left(X_c + \mu\left(x - \frac{4x^3}{3}\right) + B\right)$$

$$\dot{X_c} = \frac{\pi}{12}\left(-x\left(\frac{24}{\tau_x}\right)^2\right)$$

$$B = CI^{1/3}(1 - mX)$$

in which the drive of light on the circadian system is only in the X equation. The sensitivity function, B, includes the cube-root relationship for physical light intensity and the term −mx is included to provide a circadian modulation of the sensitivity based on the known modulation of visual sensitivity (hence m=⅓ was chosen).

In a recent modification, the light was also permitted to act on the $X_c$ equation $$\dot{X_c} = \frac{\pi}{12}\left(B(qX_c) - X\left(\frac{24}{\tau_x}\right)^2\right)$$

where q=1 was indicated at that time. It now appears that a reduced value q=0.3 or 0.4 is preferred.

A much more thorough appraisal of data has indicated two additions to the sensitivity function:

$$B = CI^{1/3}(1 - mx - kX_c - hX_c^2)$$

with k=⅓ and h=½ as preferred values. The term k $X_c$ (when combined with the original m X term) serves to advance the circadian phase at which maximum sensitivity of the circadian system to light occurs, by approximately three hours. It also increases the amount of sensitivity modulation which occurs over the circadian cycle. The term $hX_c^2$ acts to reduce sensitivity to light at circadian phases which are about ±6 hours from the nadir of the circadian cycle (which nadir is typically about 5 AM for normally entrained persons). Overall, this circadian sensitivity function is considerably different from human visual sensitivity measured throughout the day and night and reflects a current appraisal of the acute action of light on the circadian pacemaker, when it has a rhythm amplitude close to nominal (an amplitude of 1 in the mathematical model).

Finally, the action of light in the $X_c$ equation is altered by two additional terms, (a-bx)

$$\dot{X_c} = \frac{\pi}{12}\left(B(a - bx + qX_c) - X\left(\frac{24}{\tau_x}\right)^2\right)$$

where a=0.1 and b=0.1. These terms are included so that, with the corrections in the B-function just described, the phase shift observed when light is applied near the phase of the nadir of X is properly reproduced. Put another way, the original simple model did a good job when light was applied at the nadir of X but had other deficiencies. When the B-function was modified to address these deficiencies, we end up with errors for light applied at the nadir and the a-bX terms correct these.

Thus, the enhanced model is expressed by $$\dot{X} = \frac{\pi}{12}\left(X_c + \mu\left(X - \frac{4X^3}{3}\right) + B\right)$$

$$\dot{X_c} = \frac{\pi}{12}\left(B(a - bX + qX_c) - X\left(\frac{24}{\tau_x}\right)^2\right)$$

$$B = CI^{1/3}(1 - mX - kX_c - hX_c^2)$$

where:

$\tau_x$=24.2 μ=0.13 c=0.18
m=⅓ k=⅓ h=0.5
a=0.1 b=0.1 q=0.3

While the method of the present invention has been disclosed in connection with the preferred embodiment thereof, it should be understood that there are alternative realizations of the model which fall within the spirit and scope of the invention as defined by the following claims.

We claim:

1. A method of modifying a human subject's endogenous circadian cycle to a desired state, comprising the steps of:

determining the characteristics of a desired endogenous circadian cycle for said subject;

selecting an appropriate time with respect to the presumed phase of physiological markers of the subject's present endogenous circadian cycle during which to apply a light stimulus to effect a desired modification of said present endogenous circadian cycle of said subject, wherein said stimulus comprises an episode of intermittent light consisting of at least two pulses of light of enhanced intensity separated by at least one pulse of light of reduced intensity and applying said stimulus at said selected appropriate time to achieve said desired endogenous circadian cycle for said subject.

2. The method of claim 1, wherein at least one of said pulses of light of enhanced intensity has an intensity greater than approximately 4,000 lux.

3. The method of claim 1, wherein at least one of said pulses of light of enhanced intensity has an intensity between approximately 500–1,000 lux.

4. The method of claim 1, wherein at least one of said pulses of light of enhanced intensity has an intensity between approximately 1,000–2,000 lux.

5. The method of claim 1, wherein at least one of said pulses of light of enhanced intensity has an intensity between approximately 2,000–4,000 lux.

6. The method of claim 1, wherein at least one of said pulses of light of enhanced intensity has an intensity between approximately 4,000–100,000 lux.

7. The method of claim 1, wherein at least one of said pulses of light of reduced intensity has an intensity between approximately 0–200 lux.

8. The method of claim 7, wherein at least one of said pulses of light of reduced intensity has an intensity between approximately 0–10 lux.

9. The method of claim 7, wherein at least one of said pulses of light of reduced intensity has an intensity between approximately 10–50 lux.

10. The method of claim 7, wherein at least one of said pulses of light of reduced intensity has an intensity between approximately 50–200 lux.

11. The method of claim 1, wherein approximately 20% of the duration of said episode of intermittent light comprises light of enhanced intensity.

12. The method of claim 11, wherein said episode of intermittent light comprises an approximately 5 hour episode of approximately 25 minute cycles, each 25 minute cycle including approximately a 1 minute transition up to light of enhanced intensity, four minutes of enhanced light, a 1 minute transition down to light of reduced intensity, and 19 minutes of light of reduced intensity.

13. The method of claim 1, wherein greater than approximately 20% of the duration of said episode of intermittent light comprises light of enhanced intensity.

* * * * *

UNITED STATES PATENT AND TRADEMARK OFFICE
CERTIFICATE OF CORRECTION

PATENT NO.: 5,545,192
DATED : August 13, 1996
INVENTOR(S): CZEISLER et al.

It is certified that error appears in the above-identified patent and that said Letters Patent is hereby corrected as shown below:

On the title page, left column, under "[ * ] NOTICE," after "Pat.", delete the remainder of the second line and all of third line and substitute --No. 5,304,212-- therefor.

Column 6, line 8, delete equation (4) and substitute

-- $n(t) = \bar{n}(1 - e^{-(\alpha(\bar{I}) + \beta)t})$ -- therefor.

Column 6, line 10, delete equation (5) and substitute

-- $\delta(t) = \hat{C}(1 - n(t))\alpha(\bar{I}) = \hat{C}\beta\bar{n} + \hat{C}\alpha\bar{n}e^{-(\alpha(\bar{I}) + \beta)t}$ -- therefor.

Column 11, line 42, after "α" (first occurrence) insert --is--.

UNITED STATES PATENT AND TRADEMARK OFFICE
CERTIFICATE OF CORRECTION

Page 2 of 2

PATENT NO. : 5,545,192
DATED : August 13, 1996
INVENTOR(S) : CZEISLER, et. al.

It is certified that error appears in the above-indentified patent and that said Letters Patent is hereby corrected as shown below:

Column 14, line 52, delete "c=0.18" and insert --c=.018-- therefor.

Signed and Sealed this

Twenty-sixth Day of November 1996

Attest:

BRUCE LEHMAN

*Attesting Officer*     *Commissioner of Patents and Trademarks*